US012633202B2

(12) United States Patent
    Childs

(10) Patent No.: US 12,633,202 B2
(45) Date of Patent: May 19, 2026

(54) UNIVERSAL SEMI-FLUSH SMOKE DETECTOR WALL MOUNT

(71) Applicant: Richard Childs, Marstons Mills, MA (US)

(72) Inventor: Richard Childs, Marstons Mills, MA (US)

( * ) Notice: Subject to any disclaimer, the term of this patent is extended or adjusted under 35 U.S.C. 154(b) by 499 days.

(21) Appl. No.: 18/145,232

(22) Filed: Dec. 22, 2022

(65) Prior Publication Data

US 2024/0212468 A1     Jun. 27, 2024

(51) Int. Cl.
    H02G 3/08      (2006.01)
    G01N 33/00     (2006.01)
    G08B 17/10     (2006.01)

(52) U.S. Cl.
    CPC ......... G08B 17/10 (2013.01); G01N 33/0063 (2013.01)

(58) Field of Classification Search
    CPC .............................. G08B 17/10; G01N 33/0063
    See application file for complete search history.

(56) References Cited

U.S. PATENT DOCUMENTS

| | | |
|---|---|---|
| 5,333,418 A | 8/1994 | Chambers |
| 5,469,147 A | 11/1995 | Trey |
| 5,555,455 A | 9/1996 | McGinley |
| 5,808,556 A * | 9/1998 | Nelson ................. H01R 13/113 |
| | | 361/740 |
| 7,262,705 B2 | 8/2007 | Back |
| 7,504,962 B2 | 3/2009 | Smith |
| 7,778,043 B2 | 8/2010 | Rosenblatt |
| 7,969,321 B2 | 6/2011 | Spellman |
| 8,089,769 B2 | 1/2012 | Casey |
| 2008/0210839 A1 | 9/2008 | Klapp |
| 2008/0246618 A1 | 10/2008 | Siber |
| 2022/0065440 A1* | 3/2022 | Small ..................... G08B 7/066 |

FOREIGN PATENT DOCUMENTS

| | | |
|---|---|---|
| EP | 2 500 639 A2 | 9/2012 |
| EP | 2 811 083 A1 | 12/2014 |
| WO | 2009115720 A3 | 9/2009 |

* cited by examiner

*Primary Examiner* — Amy J. Sterling
(74) *Attorney, Agent, or Firm* — Lambert Shortell & Connaughton; David J. Connaughton, Jr.; Justin P. Tinger

(57)            ABSTRACT

A smoke detector wall mount is disclosed herein. In general the wall mount is a combination of several components, including, but not limited to, a bucket, a reversible trim ring, and a trim ring. The bucket may be attached within the drywall of a wall or ceiling, and a smoke detector or a combination carbon monoxide and smoke detector may be housed within the bucket. The reversible trim ring component attaches to the bucket and secures the wall mount to the wall or ceiling. Similarly, the trim ring component also attaches to the bucket and supports the weight of the smoke detector house therein. When properly installed, the smoke detector will be nearly flush with the drywall of the wall or ceiling.

12 Claims, 6 Drawing Sheets

UNIVERSAL SEMI-FLUSH SMOKE DETECTOR WALL MOUNT

BACKGROUND

Technical Field

The present disclosure relates generally to a universal semi-flush smoke detector wall mount. More particularly the present disclosure relates to a wall mount for a smoke detector or a combination smoke and carbon monoxide detector having multiple components, including a bucket, a reversible trim ring, and a trim ring.

Description of Related Art

Smoke and carbon monoxide alarms are important to have in both commercial and residential buildings alike. These alarms have sensors that detect the presence of smoke or carbon monoxide in a space. Once these harmful gases are detected, these devices may trigger an alarm, which may alert those present within the space of danger, such as a fire or gas leak. As will be appreciated by those skilled in the art, smoke and carbon monoxide detectors are required in every residential and commercial building by a combination of federal, state, and local regulations.

Carbon monoxide and smoke alarms may be battery-powered, hardwired, or a combination of both and generally must be replaced every ten (10) years. Alarms that include a combination of both smoke and carbon monoxide detectors are also known in the art; however, the carbon monoxide component of these alarms may fail before 10 years and thus may be required to be replaced sooner. Moreover, once over eleven (11) alarm devices are linked within a hardwired system, for example in a relatively large building, regulations require the switch to low voltage detectors, for which there are a variety of different types of smoke detectors available.

Therefore, what is needed is a universal semi-flush smoke detector wall mount having the following characteristics and benefits over the prior art.

SUMMARY

The subject matter of this application may involve, in some cases, interrelated products, alternative solutions to a particular problem, and/or a plurality of different uses of a single system or article.

In one aspect, a wall mount is disclosed. In this aspect, the wall mount includes a bucket, a trim ring, and a reversible trim ring. Also in this aspect, the bucket is attached to both the trim ring and the reversible trim ring.

In another aspect, a method of installing a wall mount and a smoke detector or a combination smoke and carbon monoxide detector into a ceiling is disclosed. In this aspect, the wall mount includes a bucket, a reversible trim ring and a trim ring, and the bucket has a central opening having fastener slots on its top surface. Also, in this aspect, the method includes the steps of attaching the bucket to an electrical box in the ceiling using fasteners, attaching the reversible trim ring to the bucket, and placing a smoke detector or combination smoke and carbon monoxide detector into the bucket. The method also includes the steps of connecting wiring within the electrical box to the smoke detector or the combination carbon monoxide and smoke detector and then attaching the trim ring to the bucket.

It should be expressly understood that the various physical elements of the present disclosure summarized and further disclosed herein may be of varying sizes, shapes, or otherwise dimensions and made from a variety of different materials or methods of manufacture without straying from the scope of the present disclosure.

DETAILED DESCRIPTION

Figure 1:
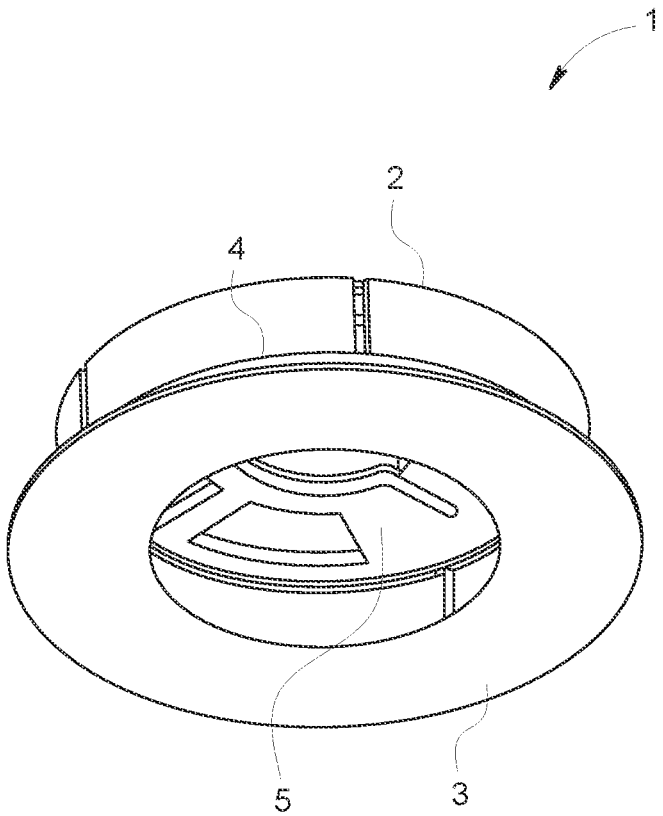
FIG. 1 provides a perspective view of an embodiment of the wall mount disclosed herein.

The detailed description set forth below in connection with the appended drawings is intended as a description of presently preferred embodiments of the invention and does not represent the only forms in which the present disclosure may be constructed and/or utilized. The description sets forth the functions and the sequence of steps for constructing and operating the invention in connection with the illustrated embodiments.

Generally, the present disclosure concerns a universal semi-flush smoke detector wall mount that may advantageously be used to mount a smoke detector or a combination carbon monoxide and smoke detector to a wall or ceiling. In most embodiments, the wall mount disclosed herein may comprise a bucket, a reversible trim ring, and a trim ring. In some embodiments, the bucket, the reversible trim ring, and the trim ring may be held together by fasteners. In other embodiments, other mechanisms may be used to connect these components. For example, in one embodiment, either the reversible trim ring, the trim ring, or both may be connected to the bucket by magnets. Furthermore, depending on the embodiment, the bucket may be sized to accommodate a variety of smoke and combination carbon monoxide and smoke detectors on the market. For example, in one embodiment, an adjustable shim may be used in combination with the bucket to hold smaller than average smoke detectors firmly within the bucket.

In a preferred embodiment, the bucket may define a plurality of slots to receive either fasteners, magnets, or some other connection component necessary to connect both the reversible trim ring and the trim ring to the bucket. For example, in one embodiment, the bucket may define a plurality of elongated fastener slots to allow the reversible trim ring to be connected to the bucket at varying depths, wherein the term "depth" is defined as the distance between either a partially closed surface of the bucket or the bucket's open face and the particular connection mechanism (e.g., fasteners, magnets, etc.). In the aforementioned embodiment, the trim ring may also be connected to the bucket through smaller slots via fasteners. However, in another embodiment, either the reversible trim ring, the trim ring, or both may be connected to the bucket by magnets.

For example, in one embodiment, a flange of either the reversible trim ring, the trim ring, or both may comprise a plurality of magnets dispersed on a surface of the flange. These magnets may connect to either a magnetic surface of the bucket or a separate plurality of magnets dispersed on a surface of the bucket. In an embodiment where magnets or a magnetic surface of either the reversible trim ring, the trim ring, or both are magnetically connected to a separate plurality of magnets on the bucket, the separate plurality of magnets on the bucket may be attached to elongated slots defined in the bucket. The elongated slots may allow the depth of the magnets to be adjusted, which may in turn allow the position of the bucket to be adjusted in relation to either the reversible trim ring or the trim ring.

One benefit of an embodiment that uses magnetic connections is that the weight of the bucket may be supported entirely by the magnetic connection between the bucket and one or both of the trim rings, thus potentially removing the need to attach the bucket to an electrical box or wall stud, as will be described further herein. Another benefit would be a potentially simplified and easier to install wall mount that may include only the bucket and one of the trim rings (i.e., a two-piece interlocking design functionality, as opposed to three or more components).

In a preferred embodiment, when the wall mount and smoke detector are properly installed within a wall or ceiling, the smoke detector is approximately flush with the drywall of the ceiling. When the term "approximately" is used herein, this term denotes a range of 0 inches to 0.75 inches, inclusive. In other words, a smoke detector that is mounted approximately flush to the drywall means 0.75 inches or less of the smoke detector protrudes below the plane of the drywall when the detector is properly installed with the wall mount in a ceiling. The smoke detector being mounted as close to flush with the ceiling as possible within the wall mount is a critical aspect of the present disclosure, as this will greatly improve the aesthetic of the smoke detector mounted on a wall or ceiling.

Furthermore, in some embodiments, after or during proper installation of the wall mount and/or smoke detector, weather stripping may be applied on the trim ring or tape may be applied over the strips or openings defined in the bucket. Additional weatherstripping, tape, and the like may be necessary to cut down on drafts. Air drafts can be extremely detrimental to the functioning of a smoke detector. Drafts from within the ceiling or elsewhere may blow smoke away from the smoke detector and prevent it from sounding the alarm. Thus, this additional feature may also be considered critical to the present disclosure.

Turning now to FIG. 1, which provides a perspective view of a presently preferred embodiment of the wall mount 1 disclosed herein, the wall mount 1 is generally formed from a bucket 2 attached to a trim ring 3. In the preferred embodiment, the bucket 2 is also attached to a reversible trim ring 4, and the bucket 2 includes an adjustable shim 5 within the interior space of the bucket 2.

Figure 2:
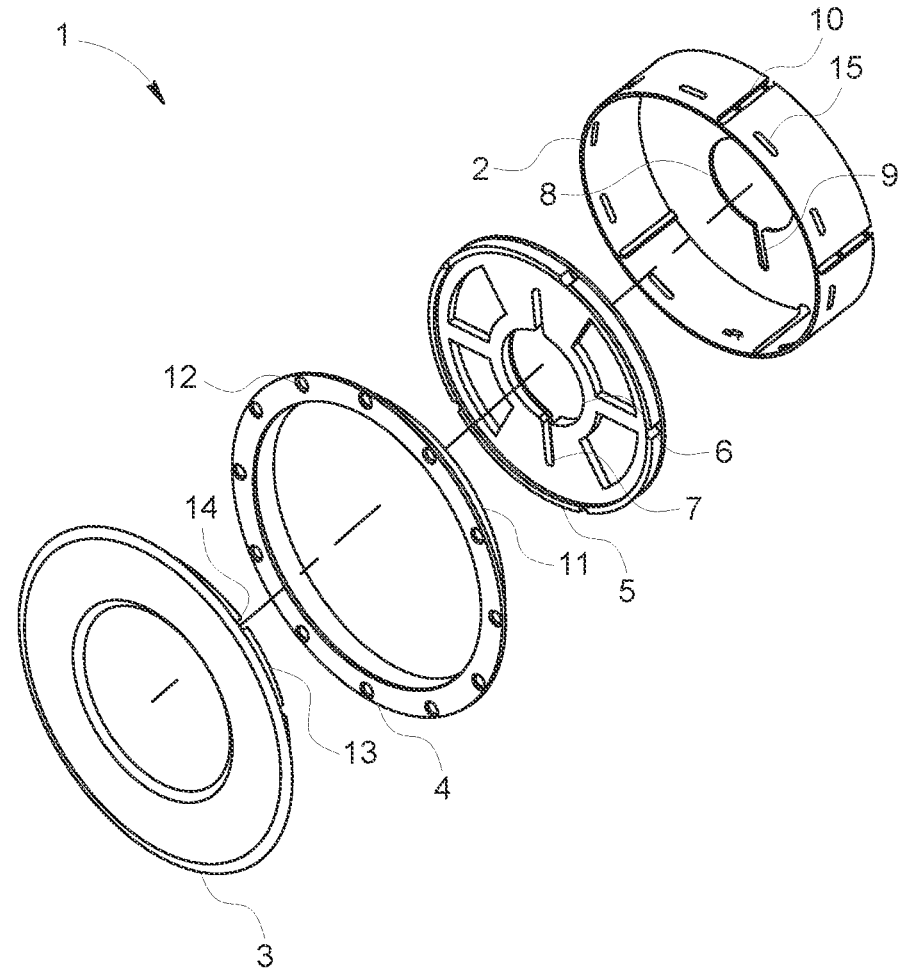
FIG. 2 provides an exploded perspective view of an embodiment of the wall mount disclosed herein.

FIG. 2 provides an exploded perspective view of the preferred embodiment of the wall mount 1 disclosed herein. In this embodiment, the adjustable shim 5 defines a central opening 6 having fastener slots 7. Similarly, the bucket 2 defines a central opening 8 and fastener slots 9 on the partially closed surface of the bucket 2. When properly assembled, the central opening 6 and fastener slots 7 of the adjustable shim 5 line up with the central opening 8 and fastener slots 9 of the bucket 2. Elongated fastener slots 10 are also defined on the exterior circumference of the bucket 2. In this embodiment, the reversible trim ring 4 attaches to the bucket 2 via screws or fasteners (not shown) that extend through the elongated fastener slots 10 through a flange 11 on one side of the reversible trim ring 4. The reversible trim ring 4 also includes a plurality of fastener holes 12. In this preferred embodiment, the fastener holes 12 are not located on the flange 11.

Figure 3:
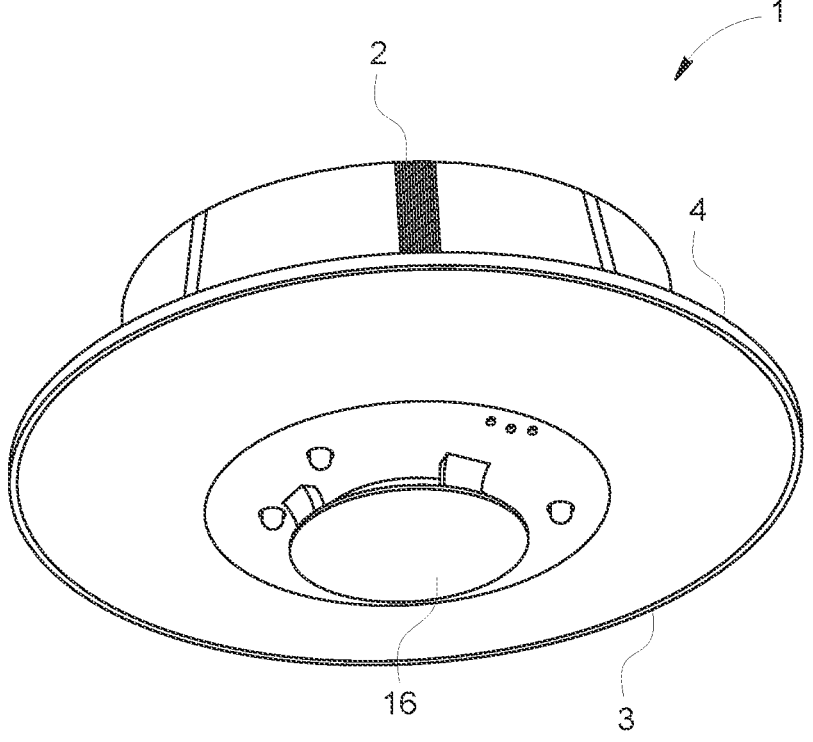
FIG. 3 provides a perspective view of an embodiment of a smoke detector housed within the wall mount disclosed herein.

Similar to the reversible trim ring 4, the trim ring 3 also includes a flange 13; however, unlike the flange 11 of the reversible trim ring 4, the flange 13 of the trim ring 3 defines a plurality of fastener slots 14. When properly assembled, screws or fasteners (shown in FIG. 6) extend through the fastener slots 14 of the trim ring 3 and the small fastener slots 15 defined on the exterior circumference of the bucket 2 and secure the trim ring 3 to the bucket 2. As shown in FIG. 3, the properly assembled wall mount 1 houses a smoke detector 16.

Depending on the embodiment, the wall mount 1 may be installed in a wall or ceiling before or after the sheetrock and/or drywall is installed. In general, the installation process includes the steps of cutting a hole in the drywall. The bucket 2 is always on the inside of the drywall, and the trim ring 3, which supports the weight of the smoke detector 16, is always on the outside or room-facing side of the wall. The position and/or location of the reversible trim ring 4 in relation to the drywall varies depending on the embodiment. When properly installed, the smoke detector 16 is close to flush with the ceiling or wall.

Figure 4:
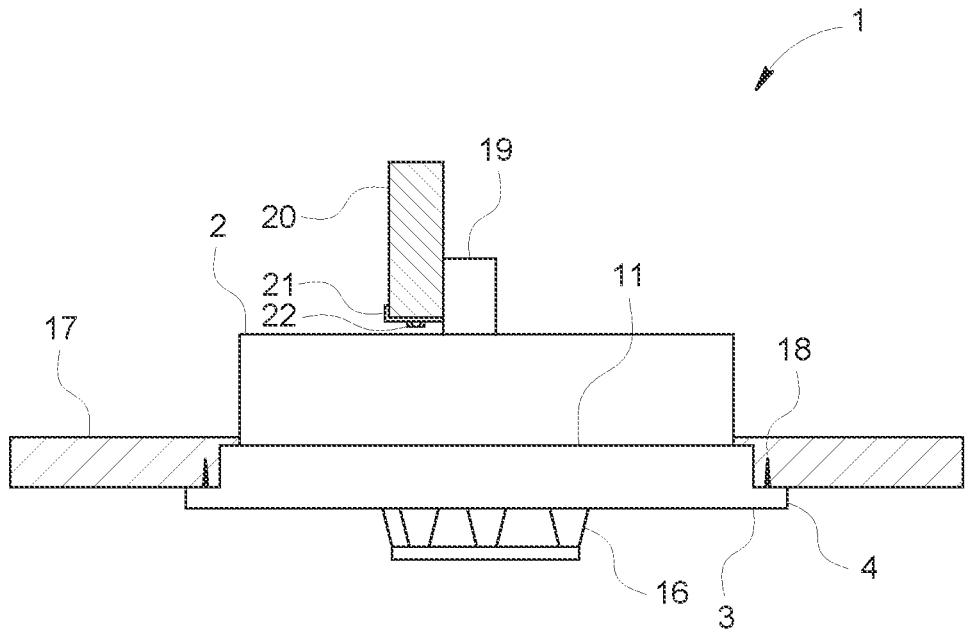
FIG. 4 provides a cross sectional perspective view of an embodiment of a smoke detector and wall mount attached to a ceiling.

Turning now to FIG. 4, which provides a cross sectional perspective view of an embodiment of a smoke detector 16 and wall mount 1 attached to a ceiling, the flange 11 of the reversible trim ring 4 is facing the inside of the hole cut in the drywall 17. In this embodiment, the reversible trim ring 4 is attached to the room-facing side of the ceiling by screws 18 twisted through fastener holes 12 (shown in FIG. 2) defined in the reversible trim ring 4 and into the drywall 17. In this embodiment, the wall mount 1 is attached to the ceiling after the drywall 17 is already in place. The weight of the smoke detector 16 is supported, at least partially, by the connection between the trim ring 3 and the bucket 2.

The bucket 2 on the inside of the ceiling wall is secured to an electrical box 19 by fasteners (not shown) extending through both the fastener slots 9 (shown in FIG. 2) on the partially closed surface of the bucket 2 and fastener holes (not shown) defined on the electrical box 19. Smoke detector wiring (not shown) within the electrical box 19 is attached to the smoke detector 16 through at least the central opening 8 defined on the partially closed surface of the bucket 2. The electrical box 19 is attached a wall stud 20 by being attached to an adjustable plate 21, wherein a bolt or screw 22 extending through both the wall stud 20 and the adjustable plate 21 secure the electrical box 19 in place. The electrical box 19 defines a track (not shown) attached to the adjustable plate 21, which allows the electrical box 19 to slide up and down relative to the wall stud 20.

Figure 5:
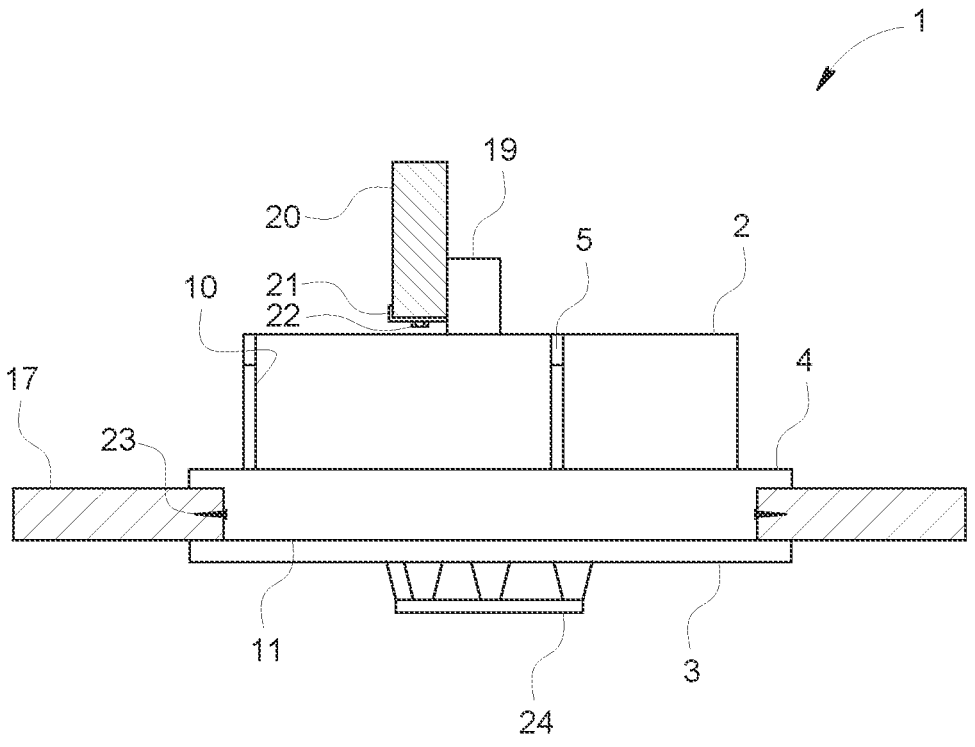
FIG. 5 provides a cross sectional perspective view of another embodiment of a smoke detector and wall mount attached to a ceiling.

FIG. 5 provides a cross sectional perspective view of another embodiment of the wall mount 1 and smoke detector 24 attached to a ceiling. In this embodiment, the bucket 2 and reversible trim ring 4 are attached to the electrical box 19 and/or the wall stud 20 of the ceiling before the drywall 17 is installed. For example, in this embodiment, the adjustable plate 21 of the electrical box 19 is first attached to the stud 20 by a screw 22. The bucket 2 is then attached to the electrical box 19 by fasteners (not shown), and the reversible trim ring 4 is attached to the bucket 2 with the flange 11 facing down (i.e., facing the outside or room-facing side of the drywall 17). Before the drywall 17 is installed, a hole is cut therein, and the hole is approximately the same size and thickness of the flange 11. After the drywall 17 is installed, the reversible trim ring 4 is secured to the bucket 2 by drilling screws 23 through the elongated slots 10 of the bucket 2, the flange 11 of the reversible trim ring 4, and, in this embodiment, into the drywall 17 of the ceiling.

After the bucket 2, reversible trim 4, and drywall 17 are installed, the smoke detector 24 is then placed inside the bucket 2 and connected to the electrical wiring (not shown) within the electrical box 19. In this embodiment, the smoke detector 24 is smaller than a standard smoke detector 16, so the adjustable shim 5 is placed inside the bucket 2 before the smoke detector 24. The trim ring 3 is then secured to the bucket 2 and supports the weight of the smoke detector 24. The adjustable shim 5 is used to ensure the smoke detector 24 fits tightly against the trim ring 3.

Figure 6:
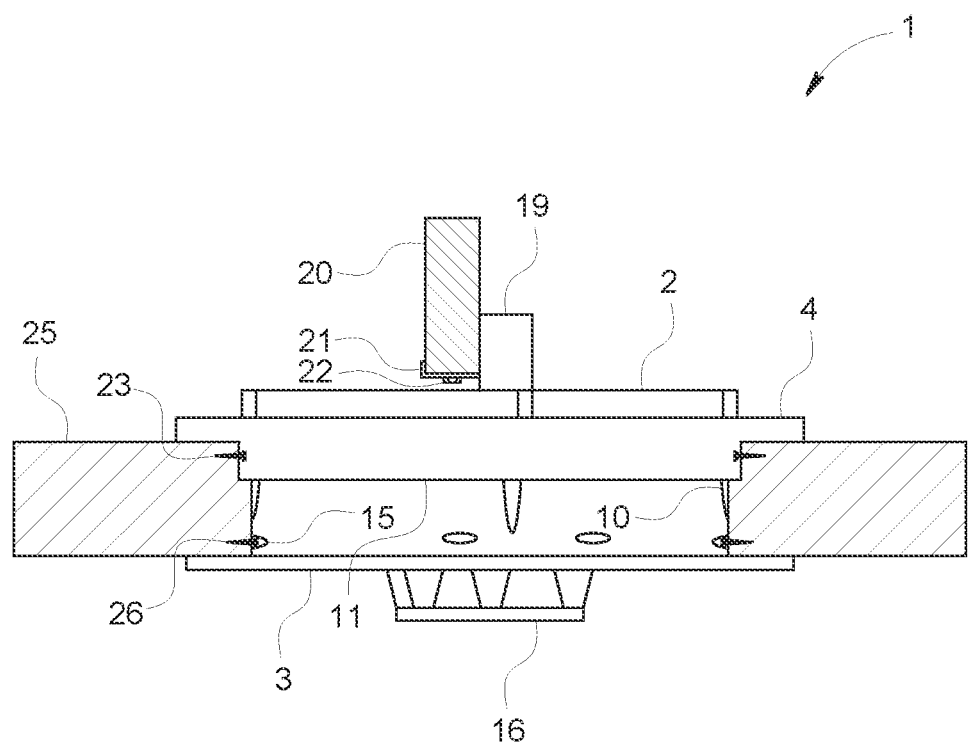
FIG. 6 provides a cross sectional perspective view of another embodiment of a smoke detector and wall mount attached to a ceiling.

Turning now to FIG. 6, which provides another cross sectional perspective view of another embodiment of a wall mount 1 and smoke detector 16 installed in a ceiling, where in this embodiment, the drywall 25 is thicker than the flange 11 of the reversible trim ring 4. Similar to the embodiment illustrated in FIG. 5, in this embodiment, at least the reversible trim ring 4 and the bucket 2 are installed before the drywall 25 by first attaching the bucket 2 to the electrical box 19 by fasteners (not shown), wherein the adjustable plate 21 of the electrical box is secured to wall stud 20 by screw 22. The reversible trim ring 4 is installed with the flange 11 facing down, and a hole is cut in the drywall 25 that is larger and/or thicker than the flange 11. The length of the elongated slots 10 allow the reversible trim ring 4 to adjust to the thickness of the drywall 25 by being secured to the bucket 2 at any point along the length of the the elongated slots 10. The reversible trim ring 4 is secured to the bucket 2 by drilling screws 23 through the elongated slots 10, flange 11, and into the drywall 25. In this embodiment, the screws 23 may be installed this way to avoid contact with the smoke detector 16 housed within the bucket 2.

After installation of the bucket 2, reversible trim ring 4, and drywall 25, the smoke detector 16 is then placed inside the bucket 2 and connected to the electrical wiring (not shown) within the electrical box 19. The trim ring 3 is then secured to the bucket 2 by drilling screws 26 through the fastener slots 14 of the trim ring 3, the small fastener slots 15 of the bucket 2, and into the drywall 25 of the ceiling. In this embodiment, similar to the screws 23 securing the reversible trim 4 to the bucket 2, the screws 26 that secure the trim ring 3 to the bucket 2 are installed this way to avoid contact with the smoke detector 16 because contact with the pointed tips of the screws 26 may scratch, damage, or even penetrate the smoke detector 16.

While several variations of the present disclosure have been illustrated by way of example in preferred or particular embodiments, it is apparent that further embodiments could be developed within the spirit and scope of the present disclosure, or the inventive concept thereof. However, it is to be expressly understood that elements described in one embodiment may be incorporated with any other embodiment in combination with any other elements disclosed herein in the various embodiments. It is also to be expressly understood that any modifications and adaptations to the present disclosure are within the spirit and scope of the present disclosure, and are inclusive, but not limited to the following appended claims as set forth.

What is claimed is:

1. A wall mount comprising:
   a bucket, a trim ring, and a reversible trim ring;
   wherein the bucket is attached to the trim ring and the reversible trim ring;
   an adjustable shim positioned within an interior space of the bucket.

2. The wall mount of claim 1 wherein the adjustable shim defines a central opening.

3. The wall mount of claim 2 wherein the central opening comprises a fastener slot.

4. The wall mount of claim 1 wherein the bucket defines a central opening on a surface of the bucket.

5. The wall mount of claim 4 wherein the central opening comprises a fastener slot.

6. The wall mount of claim 1 wherein the bucket defines a plurality of elongated fastener slots on an exterior circumference of the bucket.

7. The wall mount of claim 1 wherein the reversible trim ring comprises a flange.

8. The wall mount of claim 1 wherein the reversible trim ring defines a plurality of fastener holes.

9. A wall mount comprising:
   a bucket, a trim ring, and a reversible trim ring;
   wherein the bucket is attached to the trim ring and the reversible trim ring;
   wherein the trim ring comprises a flange; and
   wherein the flange defines a plurality of fastener slots.

10. The wall mount of claim 9 wherein the bucket defines a plurality of small fastener slots on an exterior circumference of the bucket.

11. The wall mount of claim 9 further comprising at least one of a smoke detector or a combination carbon monoxide and smoke detector housed within the bucket.

12. The wall mount of claim 11 wherein a weight of the at least one smoke detector or the combination carbon monoxide and smoke detector is supported by the trim ring attached to the bucket.

\* \* \* \* \*